United States Patent [19]
Lemasters et al.

[11] Patent Number: 6,080,730
[45] Date of Patent: *Jun. 27, 2000

[54] RINSE SOLUTION FOR ORGANS AND TISSUES

[75] Inventors: John J. Lemasters; Ronald G. Thurman, both of Chapel Hill, N.C.

[73] Assignee: The University of North Carolina at Chapel Hill, Chapel Hill, N.C.

[ * ] Notice: This patent issued on a continued prosecution application filed under 37 CFR 1.53(d), and is subject to the twenty year patent term provisions of 35 U.S.C. 154(a)(2).

[21] Appl. No.: 08/563,893

[22] Filed: Nov. 22, 1995

Related U.S. Application Data

[63] Continuation of application No. 08/105,602, Aug. 12, 1993, abandoned.

[51] Int. Cl.$^7$ .......................... A61K 31/70; A61K 31/13; A01N 1/02
[52] U.S. Cl. .................................. 514/46; 514/667; 435/1
[58] Field of Search ........................... 514/46, 662; 435/1

[56] References Cited

U.S. PATENT DOCUMENTS

| | | | |
|---|---|---|---|
| 5,066,578 | 11/1991 | Wikman-Coffelt | 435/1 |
| 5,104,859 | 4/1992 | Sollevi | 514/46 |
| 5,145,771 | 9/1992 | LeMasters et al. | 435/1 |

FOREIGN PATENT DOCUMENTS 41 33 366 A1  4/1993  Germany.

OTHER PUBLICATIONS

Gao et al., "Evidence that Adenosine Is a Key Component in Carolina Rinse Responsible for Reducing Graft Failure After Orthotopic Liver Transplanation in the Rat," *Transplantation*, 52(6), 992–998 (1991).

Currin (LeMasters) et al.(I), "Evidence that Carolina Rinse Solution Protects Sinusoidal Endothelial Cells Against Reperfusion Injury After Cold Ischemic Storage of Rat Liver, "*Transplantation*, 50(6), 1076–1077 (Dec. 1990).

Marsh et al.(I), "Hypothermic Preservation of Hepatocytes. III. Effects of Resuspension Media on Viability After Up To 7 Days of Storage," *Hepatology*, 13(3), 500–508 (1991).

Marsh et al. (II), "Glycine Prevention of Cold Ischemic Injury in Isolated Hepatocytes," *Cryobiology*, 28, 105–109 (1991).

Weinberg et al.(I), "Amino Acid Protection of Cultured Kidnay Tubule Cells Against Calcium Ionophore–Induced Lethal Cell Injury," *Laboratory Investigation*, 65(6), 671–678 (1991).

Weinberg et al.(II), "Metabolic Aspects of Protection by Glycine Against Hypoxic Injury to Isolated Promixal Tubules," *J. Am. Soc. Nephrology*, 1(7), 949–958 (1991).

Schnellmann, "Renal Mitochondrial Glutathione Transport," *Life Sciences*, 49(5), 393–398 (1991).

Schilling et al., "Membrane Stabilizing Effects of Glycine During Kidney Cold Storage and Reperfusion," *Transplantation Proceedings*, 23(5), 2387–2389 (1991).

den Butter et al.(I), "Amino Acids to Suppress Reperfusion Injury After Liver Preservation," *Transplantation Proceedings*, 23(5), 2378–2379 (1991).

Weinberg, "Glutathione and Glycine in Acute Renal Failure," *Renal Failure*, 14(3), 311–319 (1992).

Weinberg et al. (IV), "Protection of Human Umbilical Cord Vein Endothelial Cells by Glycine and Structurally Similar Amino Acids Against Calcium and Hydrogen Peroxide–Induced Lethal Cell Injury," *Am. J. Pathology*, 140(2), 457–471 (1992).

Dickson et al., "Glycine Cytoprotection During Lethal Hepatocellular Injury From Adenosine Triphosphate Depletion." *Gastroenterology*, 102(6), 2098–2107 (1992).

Marsh et al. (III), "Glycine Protects Hepatocytes from Injury Caused by Anoxia, Cold Ischemia and Mitochondrial Inhibitors, But Not Injury Caused by Calcium Ionophores or Oxidative Stress," *Hepatology*, 17(1), 91–98 (1992).

Bachmann et al. (I), "Warm Carolina Rinse Solution Prevents Graft Failure From Storage Injury After Orthotopic Rat Liver Transplantation with Arterialization," *Transplant International*, 5, 108–114 (1992).

Ferguson et al., "An Increase in Cytosolic Protease Activity During Liver Preservation," *Transplantation*, 55(3), 627–633 (1993).

den Butter et al. (II), "Effect of Glutathione and Glycine in Kidney Preservation," *Transplantation Proceedings*, 25(1), 1633–1634 (1993).

Sanchez–Urdazpal et al., "Carolina Rinse Solution Decreases Liver Injury During Clinical Liver Transplantation," *Transplantation Proceedings*, 25(1), 1574–1575 (1993).

Currin et al.(II), "Inhibition of Tumor Necrosis Factor Release From Cultured Rat Kupffer Cells by Agents that Reduce Graft Failure from Storage Injury," *Transplantation Proceedings*, 25(1), 1631–1632 (1993).

Bachmann et al. (II), "Ultrastructural Correlates of Liver Graft Failure From Storage Injury: Studies of Graft Protection by Carolina Rinse Solution and Pentoxifylline," *Transplanation Proceedings*, 25(1), 1620–1624 (1993).

Belzer et al., "Principles of Solid–Organ Preservation by Cold Storage," *Transplantation*, 45(4), 673–676 (Apr. 1988).

*Primary Examiner*—Cecilia Tsang
*Assistant Examiner*—L. Eric Crane
*Attorney, Agent, or Firm*—Myers Bigel Sibley & Sajovec, P.A.

[57] ABSTRACT

Disclosed is a rinse solution for rinsing organs and tissues prior to transplantation. The solution comprises, in one liter of solution: from 2 mM to 50 mM glycine; from 0.12 to 1.2 mM adenosine; monosaccharide, sodium, potassium, calcium and magnesium ions; and water for injection sufficient to make a liter of solution; said solution having a pH of about 6.0 to 7.5 and a concentration of potassium of less than 6 MEQ/L. Methods of making and using the solutions are also disclosed.

21 Claims, No Drawings

RINSE SOLUTION FOR ORGANS AND TISSUES

This application is a continuation of U.S. application Ser. No. 08/105,602, filed Aug. 12, 1993, and now abandoned.

The present invention was made with Government support under Grant Number DK37034 from the National Institutes of Health. The Government has certain rights to this invention.

FIELD OF THE INVENTION

This invention relates to organ transplant rinse solutions in general, and particularly relates to organ transplant rinse solutions which contain glycine.

BACKGROUND OF THE INVENTION

The introduction of cyclosporine for immunosuppression during the 1980's revived interest in transplanting organs and tissues, specifically, the liver, pancreas, heart, lung and heart-lung. However, preservation methods that are successful for kidneys have proved unsuccessful for these other organs. Until recently, the clinical preservation of the heart, liver and pancreas was kept to a minimum and to no longer than six to ten hours. Extending preservation time for these organs would have the same impact on their transplantation as it did on kidney transplantation, namely, increasing organ availability, decreasing organ wastage, increasing organ sharing, and reducing costs.

Organ transplant injury is believed to arise from two distinct components: damage induced during storage and damage resulting from reperfusion. See, e.g., G. Den Butter et al., *Transplant. Proc.* 25, 1633 (1993). Consistent with these two distinct sources of injury, two distinct types of solutions are available to extend the preservation time of organs: organ preservation solutions and organ rinse solutions.

Organ preservation solutions are used to store organs prior to transplant. An example of such a preservation solution, sometimes referred to as "University of Wisconsin" solution, is disclosed in U.S. Pat. No. 4,879,283 (see also U.S. Pat. No. 4,873,230) (available from E.I. du Pont de Nemours and Co. under the trademark VIASPAN™). Note that G. den Butter et al., supra, working with University of Wisconsin solution, conclude that glycine is protective in organ preservation and transplantation only when given to the recipient.

Organ transplant rinse solutions provide a useful compliment to organ preservation solutions. U.S. Pat. No. 5,145,771 to Lemasters and Thurman describes a solution for rinsing other preservation and storage solutions from an organ prior to implantation. This solution, referred to as "Carolina Rinse," comprises, in one liter of solution, from about 0.12 to about 1.2 mM adenosine; monosaccharide, sodium, potassium, calcium and magnesium ions; water for injection sufficient to make a liter of solution; with the solution having a pH of about 6.0 to 7.5 and a concentration of potassium of less than 6 MEQ/L.

An object of the present invention is to provide organ transplant rinse solutions with enhanced effectiveness, along with methods of using the same.

SUMMARY OF THE INVENTION

A first aspect of the present invention is an organ transplant rinse solution. The solution comprises, in one liter of solution, from 2 mM to 50 mM glycine, from 0.12 to 1.2 mM adenosine, monosaccharide, sodium, potassium, calcium and magnesium ions, and water for injection sufficient to make a liter of solution. The solution has a pH of about 6.0 to 7.5 and a concentration of potassium of less than 6 MEQ/L. The combination of these ingredients provide unique synergistic properties, as discussed in greater detail below.

A second aspect of the present invention is a solution for the rinsing of organs intended for implantation in a patient requiring such implantation prior to implantation. The solution comprises:

| | |
|---|---|
| NaCl | 85 to 145 mM |
| KCl | 3 to 6 mM |
| $CaCl_2$ | 1.0 to 1.6 mM |
| $KH_2PO_4$ | 0.7 to 1.3 mM |
| Glycine | 2.0 to 50.0 mM |
| Adenosine | 0.12 to 1.2 mM |
| Distilled deionized water | q.s. |

The solution has a pH of 6.0 to 7.4.

A third aspect of the present invention is a method of rinsing preservation or storage solution from organs or tissues intended for implantation in a patient requiring such implantation. The method comprises rinsing the organ or tissue prior (preferably immediately prior) to implantation with a rinse solution as described above. The rinse step may be preceeded by the step of maintaining the organ or tissue in a preservation or storage solution.

A further aspect of the present invention is a method of combating tissue reperfusion injury by rinsing preservation or storage solution from organs or tissues intended for implantation in a patient requiring such implantation. The method comprises rinsing the organ or tissue prior (preferably immediately prior) to implantation with a rinse solution as described above for a time and in an amount effective to combat tissue reperfusion injury. The rinse step may be preceeded by the step of maintaining the organ or tissue in a preservation or storage solution.

A still further aspect of the present invention is the use of the constituents of the solutions described above for the preparation of the rinse solutions described above.

The foregoing and other objects and aspects of the present invention are explained in detail in the specification set forth hereinbelow.

DETAILED DESCRIPTION OF THE INVENTION

Suitable organs and tissues for carrying out the present invention include, but are not limited to, liver, pancreas, kidney, lung, heart, heart valves, arteries and veins, vascular segments, ligaments and tendons, and cellular components from liver, pancreas, blood and bone marrow. Suitable recipients for practicing the invention include mammalian recipients, including both human and animal (e.g., dog, cat, horse) recipients.

The rinse solution described herein is intended for use in rinsing the preservation or storage solution from the organ or tissue prior to implantation. It can optionally be used as a preservation or storage solution, and can be used at all temperatures, from about 0° C. to normal body temperature, 37° C. Likewise, the solution may be used for perfusing tissue in situ, for example, ischemic brain, heart, limbs or bowel, namely, an organ or tissue whose circulation is blocked by a blood clot.

By rinsing the organ or tissue with the solution prior to blood reperfusion, reperfusion injury can be prevented or minimized. Rinsing may be carried out by any suitable means which brings the rinse solution in contact with the organ or tissue in place of the preservation solution, including immersion and perfusion. In general, when used as a rinse solution for combatting reperfusion injury, the solution is substantially or essentially free of oxygen (i.e., no special steps are taken to elevate the oxygen content of, or oxygenate, the solution prior to contacting the solution to the organ or tissue). Where a storage solution is employed prior to the rinsing step, any storage solution may be employed, such as those described in U.S. Pat. Nos. 4,879,283 and 4,873,230 (the disclosures of which are incorporated by reference herein in their entirety).

The potassium concentration of the described rinse solution is maintained at a physiological level, less than about six millieguivalents per liter. It is desirable that a rinse solution not have a high potassium concentration. The solution is generally sterile and essentially pyrogen-free, as will be appreciated by those skilled in the art.

Rinse solutions of the present invention may be prepared as described in U.S. Pat. No. 5,145,771 to Lemasters and Thurman (the disclosure of which is to be incorporated by reference herein in its entirety), with the formulation described therein modified to include from 2 mM to 50 mM glycine. As one embodiment of the described invention, the rinse solution contains glycine as noted above, about 3 mM glutathione, 1 mM adenosine, 10 mM glucose, and sodium, potassium, calcium and magnesium ions, and a pH of 6.5. 2 $\mu$M of a calcium blocking agent such as nicardipene can be added. Other suitable blocking agents are nifedipine, diltiazem or verapamil. Fructose can replace the glucose. Ribose and adenine, together, can replace the adenosine. Preferably, the solution also contains about 5% hydroxyethyl starch, as described hereinafter.

A suitable colloid is a modified hydroxyethyl starch having a weight average molecular weight of about 50,000 to one million daltons. A preferred hydroxyethyl starch is one having a molecular weight of from about 150,000 to about 350,000 daltons and degree of substitution of from about 0.4 to about 0.7. A more preferred colloid is hydroxyethyl starch having a weight average molecular weight of from about 200,000 to about 300,000 daltons. The preferred colloid is substantially free of hydroxyethyl starch having a molecular weight of less than about 50,000 daltons. In accordance with one embodiment of the present invention, the hydroxyethyl starch is dialyzed against distilled-deionized water or otherwise treated to remove contaminants which have an adverse affect on the effectiveness of hydroxyethyl starch preparations. The materials removed by the dialysis process are the very smallest hydroxyethyl starch components, including the ethylene glycol and ethylene chlorohydrin side products of the hydroxyethylation as well as the residual acetone and sodium chloride. Other suitable, but less preferred, colloids are albumin, dextran, polyethylene glycol and polyvinyl pyrolidone.

In a preferred embodiment, the rinse or preservation solution composition includes, but is not limited to, the components in about the concentration ranges set forth in Table 1 below. As noted above, the hydroxyethyl starch is optional but preferred.

TABLE 1

Concentration Ranqes in 1 Liter

| | |
|---|---|
| 10% modified hydroxyethyl starch | 30 g/L to 100 g/L |
| NaCl | 85 mm to 145 mM |
| KCl | 3 mM to 6 mM |
| CaCl$_2$ | 1.0 mM to 1.6 mM |
| KH$_2$PO$_4$ | 0.7 mM to 1.3 mM |
| MgSO$_4$ | 0.9 mM to 1.5 mM |
| Allopurinol | 0.05 mM to 5 mM |
| Desferrioxamine | 0.02 mM to 2.0 mM |
| Glutathione | 0.5 mM to 10.0 mM |
| Nicardipene | 0.1 $\mu$M to 5 $\mu$M |
| Adenosine | 0.1 mM to 5 mM |
| Glycine | 2 mM to 50 mM |
| Fructose | 1 mM to 50 mM |
| Glucose | 1 mM to 50 mM |
| Insulin | 5 U/L to 250 U/L |
| Mops | 2 mM to 40 mM |

The following examples are intended to be illustrative of the present invention but should not be considered as limiting the scope thereof.

EXAMPLE 1

Preparation of Glycine-Containing Rinse Solution

A preferred embodiment of a Carolina Rinse solution containing glycine is prepared with the components in the amounts set forth in Table 2 below in accordance with the instructions set forth below.

TABLE 2

Components of 1 Liter Rinse Solution

| | | |
|---|---|---|
| 500 mL | Distilled Deionized Water | |
| 50 g/L | 10% modified hydroxyethyl starch | |
| 115 mM | NaCl | 6.7 g |
| 5 mM | KCl | 0.37 g |
| 1.30 mM | CaCl$_2$ | 0.19 g |
| 1 mM | KH$_2$PO$_4$ | 0.14 g |
| 1.2 mM | MgSO$_4$ | 0.15 g |
| 1 mM | Allopurinol | 0.14 g |
| 1 mM | Desferrioxamine | 0.65 g |
| 3 mM | Glutathione | 0.92 g |
| 2 $\mu$M | Nicardipene | 0.80 mg |
| .2 mM | Adenosine | .064 g |
| 5 mM | Glycine | .375 g |
| 10 mM | Fructose | 1.8 g |
| 10 mM | Glucose | 1.8 g |
| 100 U/L | Insulin | 100 units |
| 20 mM | Mops | 4.2 g |

Using a 500 mL volumetric flask, measure 500 mL of 10% (weight/volume) hydroxyethyl starch solution and pour into a 1 L beaker. Add 400 mL of double distilled water and stir vigorously using a magnetic stir bar. Add the rest of the components one at a time. After all components are are added, adjust the pH to 6.5 with 1–2 mL 5 N NaOH. The solution should be stirred for at least thirty minutes. Transfer the solution to a 1 L volumetric flask and bring to 1 L final volume. Filter to remove any undissolved particles. After sterile filtration the solution is ready. This preparation is hereinafter referred to as "Carolina Rinse," with or without glycine, depending on whether or not the glycine component is included therein.

EXAMPLE 2

In Vitro Materials and Methods

To evaluate the efficacy of Carolina rinse solution in prevention of lethal reperfusion injury to endothelial cells, rat livers were stored and reperfused as described previously (J. Caldwell-Kenkel et al., *Transplantation* 45, 834 (1988); J. Caldwell-Kenkel et al., *Hepatology* 10, 292 (1989)). Briefly, livers of male Sprague-Dawley rats (200–300 g) were perfused via the portal vein at 3–4 ml/min/g with Krebs-Henseleit bicarbonate buffer saturated with 95% oxygen, 5% carbon dioxide in a nonrecirculating system. After 20 min., the livers were flushed with ice-cold University of Wisconsin solution (DuPont, Wilmington, Del.) supplemented with penicillin (2000,000 U/L), insulin (40 U/L), and dexamethasone (16 mg/L) for 2 min (F. Belzer and H. Southard, *Transplantation* 45, 673 (1988)). Livers were then removed from the perfusion block, immersed in University of Wisconsin solution, and placed in sealed plastic containers surrounded by ice slush. After storage intervals of 24 or 96 hr. livers were perfused again with oxygen-saturated Ringer's solution (control), Ringer's solution with 5 mM glycine (glycine), Carolina rinse solution (CR), or Carolina rinse solution with 5 mM glycine (CR-glycine) at 37° C. Livers were reperfused initially at flow rates of 0.5–1 ml/min/g, values that were gradually increased to about 3–4 ml/min/g over 5 min. After 10 min, 500 μM trypan blue was added to the reperfusion medium, and after 5 more min the livers were fixed with 2% paraformaldehyde, 2% glutaraldehyde in 0.1 M NaPi buffer, pH 7.4. Subsequently, the tissue was embedded in water-soluble glycol methacrylate, sectioned, and stained with eosin. Trypan blue positive nuclei of nonviable nonparenchymal cells were counted in 6 random periportal and pericentral fields as a percent of total nonparenchymal cell nuclei tallied in tissue sections stained with methylene blue-acid fuchsin. Previous studies showed that nuclear labeling with cell-impermeant, DNA-intercalating dyes such as trypan blue is a valid criterion of loss of cell viability after hypoxic injury (B. Bradford et al., *Pharmacol. Exp. Ther.* 236, 263 (1986); B. Herman et al., *FASEB J* 2: 146 (1988)).

EXAMPLE 3

In vitro Protective Effect of Glycine and Carolina Rinse in Combination

This experiment was carried out to determine the in vitro protective effect of Carolina Rinse, with and without glycine, on nonparenchymal cells. Carolina Rinse was prepared as described in Example 2 above; the experiment was carried out as described in Example 1 above. Results are summarized in Table 3 below. The data are means±S.E.M. with the number of experiments for each group being given in parentheses. After 24 hours of storage, CR and glycine each reduced reperfusion induced nonparenchymal cell killing substantially. After 48 hours of storage, CR and glycine each partially prevented cell killing. By contrast, The combination of CR and glycine virtually eliminated lethal cell killing.

TABLE 3

Protection Against Reperfusion-Induced Nonparenchymal Cell Killing to Rat Livers Stored for Transplantation Surgery by Carolina Rinse (CR), Glycine, or CR plus Glycine.

| Rinse Solution | Storage Time | Nonparenchymal Cell Killing |
|---|---|---|
| Control | 24 h | 23.6 ± 3.2 (12) |
| CR | 24 h | 1.0 ± 0.3 (11) |
| Glycine | 24 h | 1.4 ± 0.4 (6) |
| Control | 48 h | 29.40 ± 4.4 (5) |

TABLE 3-continued

Protection Against Reperfusion-Induced Nonparenchymal Cell Killing to Rat Livers Stored for Transplantation Surgery by Carolina Rinse (CR), Glycine, or CR plus Glycine.

| Rinse Solution | Storage Time | Nonparenchymal Cell Killing |
|---|---|---|
| CR | 48 h | 7.0 ± 0.8 (5) |
| Glycine | 48 h | 8.6 ± 2.2 (5) |
| CR-Glycine | 48 h | 1.6 ± 0.3 (6) |

EXAMPLE 4

In Vivo Materials and Methods

Livers of syngeneic male Lewis rats (250–300 g) were transplanted under ether anesthesia essentially as described by R. Steffen et al., *Transplantation* 48, 166 (1989). In the donor operation, the donor liver was flushed via the portal vein with chilled UW solution. The superior vena cava, inferior vena cava, portal vein, celiac artery near the aorta, and bile duct were divided and the liver was excised. Cuffs were placed on the portal vein and inferior vena cava, and the liver was stored in UW solution in an ice-water bath for up to 30 hours. In recipient rats, the hepatic and gastroduodenal arteries were divided between ligatures at their origin, leaving a stump of the common hepatic artery. The stump was clamped at the base of the dissected segment and cut at the bifurcation of the hepatic and gastroduodenal arteries. This procedure left a funnel-shaped opening to which a cuff was attached. After dividing the bile duct at the hilum, the superior vena cava, inferior vena cava, and portal vein were clamped and divided and the recipient liver was removed. The donor liver was then rinsed with 15 mls of various rinse solutions and placed in the abdomen. The temperature of the rinse solutions was 37° C. Subsequently, the superior vena cava was anastomosed with a running suture and the portal vein, inferior vena cava, and hepatic artery were connected in sequence by insertion of cuffs. The bile duct was anastomosed over an intraluminal polyethylene splint. Implantation surgery required 60 min. During the time, the portal vein was clamped for 15 min and the inferior vena cava for no more than 20 min. Rats were given food and water ad libitum postoperatively.

Both long-term survival and average hours of survival are used as indices of experimental outcome, in accordance with known techniques. See, e.g., Y. Takei et al., *Transplantation* 52, 225 (1991). Long-term survival was defined as the percent or fraction of rats living 30 days postoperatively, a time after which indefinite survival was virtually assured. Average hours of survival, in contrast to percent long-term survival, provided a discriminating measure of outcome for treatments in which animals did not survive 30 days. After 30 days, all transplant recipients were sacrificed.

EXAMPLE 5

In vivo Protective Effect of Glycine and Carolina Rinse in Combination

These experiments were carried out in accordance with the procedures described in Example 4 above. Long term (30 day) survival data are given in Table 4 below; survival time in hours for rats which did not survive to 30 days is given in Table 5 below. In each table, the storage time of the transplanted liver in University of Wisconsin Solution is given in hours in the leftmost column thereof.

TABLE 4

Long Term Survival of Rats Implanted with Livers Rinsed with Carolina Rinse (CR) or Ringer's Solution with and without Glycine.

| Storage Time | CR | CR + Glycine | Ringers | Ringers + Glycine |
|---|---|---|---|---|
| 18 hrs | 3/4 | 4/5 | 4/4 | 3/3 |
| 21 hrs | — | 4/5 | 1/2 | 2/2 |
| 24 hrs | 0/6 | 6/12 | 0/6 | 1/7 |
| 30 hrs | 0/1 | 0/1 | — | — |

TABLE 5

Hours of Survival of Rats which Died Within 30 Days After Implantation with Livers Rinsed with Carolina Rinse (CR) or Ringer's Solution with and without Glycine.

| Storage Time | CR | CR + Glycine | Ringers | Ringers + Glycine |
|---|---|---|---|---|
| 18 hrs | 48 ± 0 | 65 ± 0 | — | — |
| 21 hrs | — | 45 ± 0 | 20 ± 0 | — |
| 24 hrs | 24 ± 1.0 | 41 ± 21.5 | 20 ± 5.8 | 36 ± 24.9 |
| 30 hrs | 20 ± 0 | 40 ± 0 | — | — |

Note particularly in Table 4 that 6 of 12 animals survived implantation with livers stored for 24 hours in University of Wisconsin solution, when the organs were rinsed with Carolina Rinse containing glycine. In contrast, zero of 6 animals survived when the organ was rinsed with Carolina Rinse alone, and only 1 of 7 animals survived when the organ was rinsed with Ringer's solution containing glycine. These data again indicate that Carolina Rinse with Glycine provides a superior protective effect to either Carolina Rinse without glycine, or Ringer's solution with glycine.

The foregoing Examples are illustrative of the present invention, and are not to be taken as limiting thereof. The invention is defined by the following claims, with equivalents thereof to be included therein.

That what is claimed is:

1. An organ transplant rinse solution composition comprising, in one liter of solution: from 2 mM to 50 mM glycine; from 0.12 to 1.2 mM adenosine; a monosaccharide; sodium, potassium, calcium and magnesium ions; and water for injection sufficient to make a liter of solution; said solution composition having a pH of about 6.0 to 7.5 and a concentration of potassium of less than 6 MEQ/L.

2. The solution composition of claim 1, essentially free of oxygen.

3. The solution composition of claim 1, wherein glycine is included in an amount of 5 mM.

4. A solution composition according to claim 1, further comprising about 5% by weight of hydroxyethyl starch, said hydroxyethyl starch having a weight average molecular weight of from about 50,000 to about 1,000,000 daltons.

5. A solution composition according to claim 1, having a pH of 6.5.

6. A solution composition according to claim 1, further comprising from 0.05 to 5 mM allopurinol.

7. A solution composition according to claim 1, further comprising 0.5 to 10 mM glutathione.

8. A solution composition according to claim 1, further comprising 0.1 to 5 mM nicardipine.

9. A solution composition according to claim 1, further comprising 0.02 to 2 mM desferrioxamine.

10. A solution composition for the rinsing of organs intended for implantation prior to said implantation in a patient requiring such implantation, said solution composition comprising:

| | |
|---|---|
| NaCl | 85 to 145 mM |
| KCl | 3 to 6 mM |
| $CaCl_2$ | 1.0 to 1.6 mM |
| $KH_2PO_4$ | 0.7 to 1.3 mM |
| Glycine | 2.0 to 50.0 mM |
| Adenosine | 0.12 to 1.2 mM |
| Distilled deionized water | q.s. | and said solution having a pH of 6.0 to 7.4.

11. The solution composition of claim 10, essentially free of oxygen.

12. The solution composition of claim 10, wherein glycine is included in an amount of 5 mM.

13. A solution composition according to claim 10, further comprising about 5% by weight of hydroxyethyl starch, said hydroxyethyl starch having a weight average molecular weight of from about 50,000 to about 1,000,000 daltons.

14. A solution composition according to claim 10, having a pH of 6.5.

15. A solution composition according to claim 10, further comprising from 0.05 to 5 mM allopurinol.

16. A solution composition according to claim 10, further comprising 0.5 to 10 mM glutathione.

17. A solution composition according to claim 10, further comprising 0.1 to 5 mM nicardipine.

18. A solution composition according to claim 10, further comprising 0.02 to 2 mM desferrioxamine.

19. A method for rinsing preservation or storage solution from organs or tissue intended for implantation in a patient requiring such implantation, said method comprising:

rinsing said organ or tissue prior to implantation with a solution comprising, in one liter of solution:

from 2 mM to 50 mM glycine; from 0.12 mM to 1.2 mM adenosine; sodium, potassium, calcium and magnesium ions; and water for injection sufficient to make a liter of solution;, said solution having a pH of about 6.0 to 7.5 and a concentration of potassium of less than 6 MEQ/L.

20. A method according to claim 19, wherein said organ or tissue is selected from the group consisting of liver, pancreas, kidney, lung, heart, heart valve, artery, vein, vascular segments, ligaments, tendons, and cellular components from liver, pancreas, blood and bone marrow.

21. A method according to claim 19, wherein said solution is essentially free of oxygen.

* * * * *

UNITED STATES PATENT AND TRADEMARK OFFICE
CERTIFICATE OF CORRECTION

PATENT NO. : 6,080,730                                      Page 1 of 2
DATED      : June 27, 2000
INVENTOR(S) : Lemasters et al.

It is certified that error appears in the above-indentified patent and that said Letters Patent is hereby corrected as shown below:

On the title page: Item [56]

Please insert,

OTHER PUBLICATIONS

"Weinberg et al.(I), "Amino Acid Protection of Cultured Kidnay Tubule Cells Against Calcium Ionophore-Induced Lethal Cell Injury," *Laboratory Investigation*, 65(6), 671-678 (1991)."

should read

--Weinberg et al.(I), "Amino Acid Protection of Cultured Kidney Tubule Cells Against Calcium Ionophore-Induced Lethal Cell Injury," *Laboratory Investigation*, 65(6), 671-678 (1991).--

--G. Den Butter et al.; *Effect of Glycine in Dog and Rat Liver Transplantation*; Transplantation; 56: 817-822, (Oct. 1993)

UNITED STATES PATENT AND TRADEMARK OFFICE
CERTIFICATE OF CORRECTION

PATENT NO. : 6,080,730
DATED : June 27, 2000
INVENTOR(S) : Lemaster et al

Page 2 of 2

It is certified that error appears in the above-indentified patent and that said Letters Patent is hereby corrected as shown below:

M. Schilling et al.; *Glycine Prevents Hydroxyl Radical, Ca++, and Phospholipase A2 Induced Reperfusion Injury in Renal Preservation*; Chir. Forum Exp. Klin. Forsch., no. 1:373-376 (1992)

A. Saunder et al.; *Cytoprotective Effect of Glycine in Cold Stored Canine Renal Tubules*; Cryobiology, 30:243-249 (June 1993)

Weinberg et al. (V), "Cytoprotective Effects of Glycine and Glutathione Against Hypoxic Injury to Renal Tubules," *Journal of Clinical Investigation*, 80(11), 1446-1454 (November, 1987).--

Signed and Sealed this

Seventeenth Day of April, 2001

*Attest:*

NICHOLAS P. GODICI

*Attesting Officer*  *Acting Director of the United States Patent and Trademark Office*